United States Patent
Zhadanov et al.

(10) Patent No.: US 9,259,301 B2
(45) Date of Patent: Feb. 16, 2016

(54) DOUBLE ACTING PULSATING TIP JET

(71) Applicants: Eli Zhadanov, Brooklyn, NY (US); Sam Zhadanov, Brooklyn, NY (US)

(72) Inventors: Eli Zhadanov, Brooklyn, NY (US); Sam Zhadanov, Brooklyn, NY (US)

(*) Notice: Subject to any disclaimer, the term of this patent is extended or adjusted under 35 U.S.C. 154(b) by 0 days.

(21) Appl. No.: 14/251,885

(22) Filed: Apr. 14, 2014

(65) Prior Publication Data
US 2015/0289957 A1    Oct. 15, 2015

(51) Int. Cl.
*A61C 17/02*    (2006.01)
*A61H 13/00*    (2006.01)

(52) U.S. Cl.
CPC .......... *A61C 17/0202* (2013.01); *A61H 13/005* (2013.01)

(58) Field of Classification Search
CPC ............. A61C 17/028; A61C 17/0211; A61C 17/0202; A61C 17/02
USPC .................................................. 601/162, 163
See application file for complete search history.

(56) References Cited

U.S. PATENT DOCUMENTS

| | | | |
|---|---|---|---|
| RE26,589 E * | 5/1969 | Murov et al. ................. | 15/22.1 |
| 3,496,933 A * | 2/1970 | Lloyd ........................... | 601/162 |
| 3,509,874 A * | 5/1970 | Stillman ....................... | 601/163 |
| 5,484,281 A * | 1/1996 | Renow et al. ................. | 433/80 |
| 6,245,032 B1 * | 6/2001 | Sauer et al. .................. | 601/162 |
| 6,918,153 B2 * | 7/2005 | Gruber .......................... | 15/22.1 |
| 7,059,853 B2 * | 6/2006 | Hegemann ..................... | 433/80 |
| 7,934,272 B2 * | 5/2011 | Zhadanov et al. ............. | 4/448 |
| 2003/0171704 A1 * | 9/2003 | McNair ......................... | 601/163 |

FOREIGN PATENT DOCUMENTS

EP           0 097 015 A2 * 12/1983

* cited by examiner

*Primary Examiner* — Ralph Lewis
(74) *Attorney, Agent, or Firm* — Henry M. Feiereisen LLC

(57) ABSTRACT

With a device and a method of treatment of gums and teeth, two pulsating fluid jets are directed to two opposite sides of a gum or teeth and can include two pulsating jets of a carbonated fluid.

7 Claims, 2 Drawing Sheets

DOUBLE ACTING PULSATING TIP JET

BACKGROUND OF THE INVENTION

The present invention relates to devices and methods for acting on gums and teeth.

Various apparatuses and methods are used for these purposes. Some vibrating devices are used to apply a mechanical vibration to the gums. Devices provided for cleaning tools are used to clean teeth pockets. It is believed that the known devices, apparatuses and methods can be further improved to provide a simple and efficient massaging of gums and cleaning of teeth pockets.

SUMMARY OF THE INVENTION

Accordingly, it is an object of the present invention to provide a device and a method for acting on gums and teeth, which are further improvements of existing apparatuses and methods.

In keeping with these objects and with others which will become apparent hereinafter, one feature of the present invention resides, briefly states, in device for acting on gums and teeth, comprising a hollow body having an inner passage for supplying a fluid, a head connected with the hollow body and having an inner chamber with two outlet openings, and a rotor having a plurality of vanes and arranged in the inner chamber of the head and rotatable under the action of the fluid flowing through the inner passage of the body and the inner chamber of the head and issuing from the outlet openings of the head in form of two pulsating fluid jets so as to act on a gum or teeth from both sides thereof.

When the device is designed and the method is performed according to the present invention, a very efficient treatment of gums and teeth is provided.

In accordance with another feature of the present invention the axis of the inner passage in the body which supplies the fluid into the head is parallel to the axis extending through the two outlet openings of the head.

In accordance with a further feature of the present invention the inner passage of the body extends tangentially relative to the inner chamber of the head, so that fluid is supplied into the inner chamber of the head tangentially to the rotor.

In accordance with still another feature of the present invention, in the device according to the present invention, the body has an upper side, and a cover which closes the upper side of the body.

In accordance with a further feature of the device according to the present invention, a partition is provided at a lower side of the rotor so as to cover for example two vanes of the rotor from below.

A still further feature of the present invention resides in a method of acting on gums and teeth, comprising the steps of treating gums and/or teeth by acting on gums and/or teeth from two opposite sides by two pulsating fluid jets.

The novel features of the present invention are described in detail in the following description of the preferred embodiments, which is accompanied by the following drawings.

DESCRIPTION OF THE PREFERRED EMBODIMENTS

Figure 1:
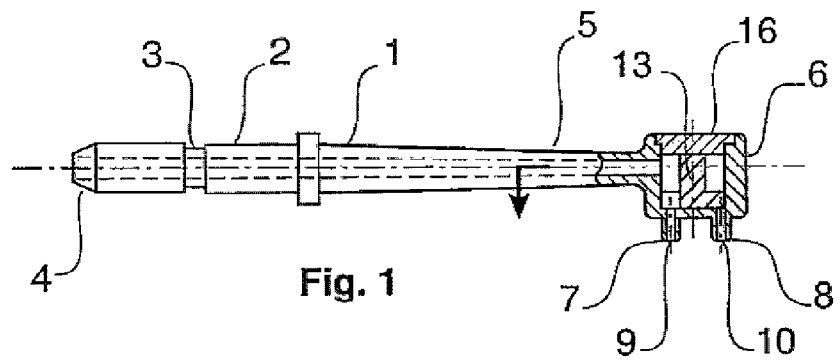
FIG. 1 of the drawings is a view showing a cross section in a first plane of a device for acting on gums and teeth in accordance with present invention.
Figure 3:
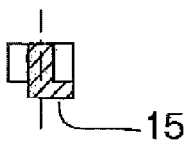
FIG. 3 is a vertical cross section of a rotor with vanes of the device according to the present invention.

A device for acting on gums and teeth according to the present invention has a hollow elongated body 1 provided on one end with a cylindrical portion 2 with a groove 3 and a conical end 4 for introducing in an apparatus as will be explained hereinbelow. The body 1 has a hollow conical portion 5 having an inner conical passage. The elongated body 1 is connected with a substantially cylindrical head 6 provided with two hollow projection 7 and 8 which have inner openings 9 and 10.

Figure 2:
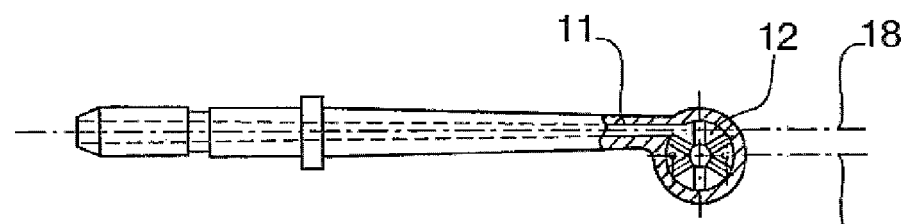
FIG. 2 is a view showing a cross section in a second plane of the device for acting on gums and teeth in accordance with the present invention.
Figure 4:
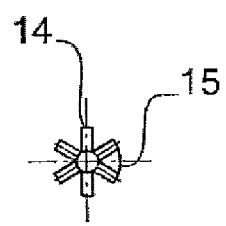
FIG. 4 is a top view of the rotor with vanes as seen in an axial direction of the device according to the present invention.

As can be seen from FIGS. 1 and 2, the inner passage 11 of the hollow body 1 has a first axis 18, and the fluid is supplied from the inner passage 11 of the hollow body 1 into the head 6 in direction of the first axis 18. The opening 9 and 10 are provided on opposite sides of an axis of the head 6 and located on an axis 17 which is parallel to the axis 18.

In the device according to the invention the head 6 is connected to the body 1 along a tangent, or in other words tangentially. In particular, the inner passage 11 of the body 1 is connected with the inner chamber 12 of the head 6 tangentially. The axis 18 of the inner passage 11 of the head extends parallel to the axis 17 extending through the openings 9 and 10. A rotor 13 is rotatably arranged in the inner chamber 12 of the head 6. It has a plurality of vanes 14. In the lower part of the rotor 13 it is provided with a partition 15 which overlaps for example two vanes 14. The upper open end of the head 6 is closed by a cover 16.

Figure 5:
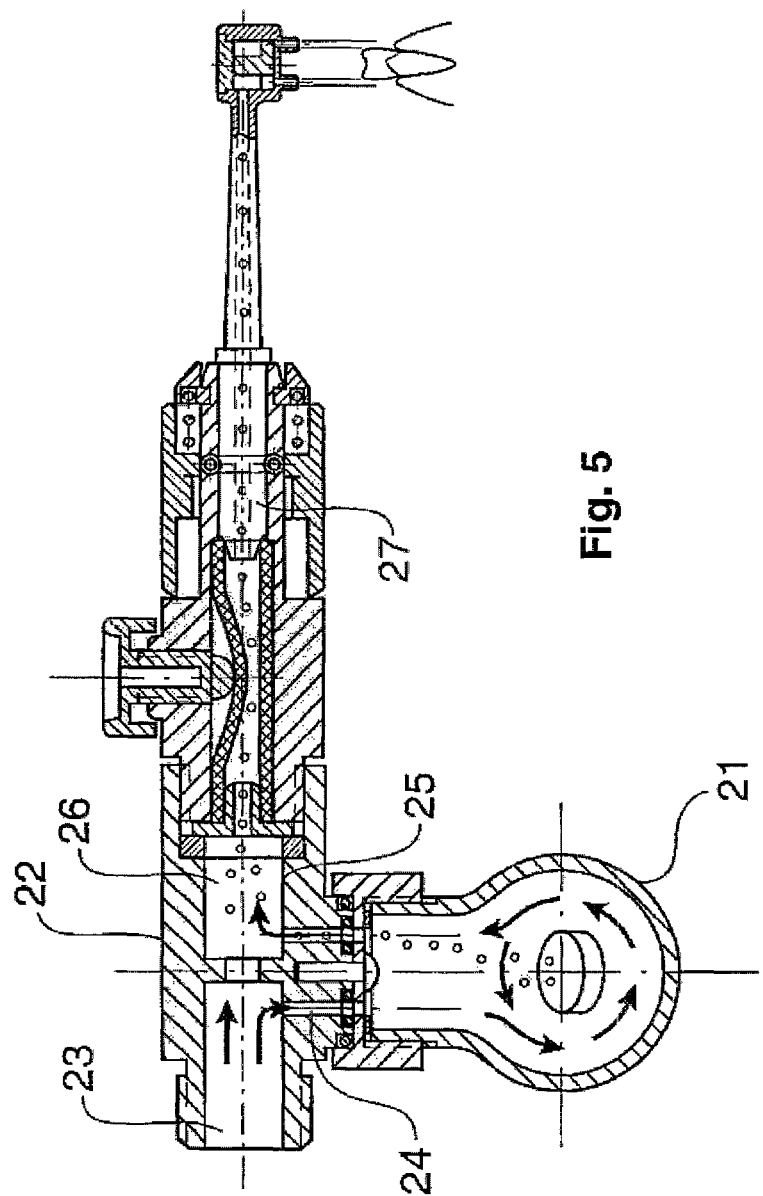
FIG. 5 is a view showing the inventive device connected with an apparatus for producing a carbonated solution.

The device in accordance with the present invention can operate in cooperation with an apparatus shown in FIG. 5. The apparatus has a vessel 21 for accommodating tablets which are dissolvable in water and form a carbonated fluid or a carbonated solution in water, such as for example Alka-Selzer and the like. The vessel 21 can be spherical and is attachable to a housing 22 of the apparatus with interposition of seals, and detachable from it for example via threads. A water supplying element 23 is connectable to a source of water and supplies water through an inlet passage 24 into the vessel 21 in which a carbonated solution is formed. The carbonated solution is then supplied from the vessel 21 through an outlet passage 25 of the vessel 21 and further through a central channel 26 of the housing 22 of the apparatus into the device of the present invention.

The construction of the apparatus is disclosed in general in our U.S. Pat. No. 7,934,272 which is issued on May 3, 2011 and incorporated here by reference and whose other components therefore are not described here in detail.

The carbonated fluid which is formed in the apparatus flows through the outlet passage 15 of the apparatus into the inner passage 11 of the elongated body 1 of the inventive device and then into the inner chamber 12 of the head 6 tangentially to the rotor 13. It rotates the rotor around its axis, and issues outwardly through the openings 9 and 10 of the head 6 in form of two pulsating fluid jets, which can act on both sides of a gum and/or teeth in a pulsating manner so as to provide a very efficient treatment of gums and teeth.

The present invention is not limited to the details shown since further modifications and structural changes are possible without departing from the spirit of the invention.

What is desired to be protected by Letters Patent is set forth in particular in the appended claims.

The invention claimed is:

1. A device for acting on gums and teeth, comprising:
   an elongated tubular hollow body having an inner passage for supplying a fluid;
   a head connected with the elongated tubular hollow body and having an inner chamber with an axis and with only two outlet openings; and
   a rotor having a plurality of vanes and arranged in the inner chamber of the head rotatably about an axis which is coaxial with the axis of the inner chamber of the head, so that the fluid flowing from the inner passage of the elongated tubular hollow body into the inner chamber of the head rotates the rotor and issues from the only two outlet openings of the head in form of only two pulsating fluid jets to act on a gum and teeth from two opposite sides,
   wherein the inner passage of the elongated tubular hollow body has a first axis, so that the fluid flows from the inner passage of the elongated tubular hollow body into the head in direction of the first axis,
   wherein the only two openings of the head are provided at opposite sides of the axis of the head and located on a second axis which extend parallel to the first axis.

2. The device for acting on gums and teeth as defined in claim 1, wherein the elongated body is connected to the head so that the elongated body is tangential to the head.

3. The device for acting on gums and teeth as defined in claim 1, wherein the inner passage of the hollow body extends tangentially to the inner chamber of said head and tangentially to the rotor so that the fluid flows from the inner passage of the elongate body into the inner chamber of the head tangentially to the rotor.

4. The device for acting on gums and teeth as defined in claim 1, wherein said inner passage of said elongated body is configured conical and narrows in a direction toward the inner chamber of the body.

5. The device for acting on gums and teeth as defined in claim 1, further comprising a partition provided under at least some of the vanes of the rotor located in the inner chamber of the head.

6. The device for acting on gums and teeth as defined in claim 1, wherein the head has an upper open end, further comprising a cover which covers the upper open end of the head.

7. The device for acting on gums and teeth as defined in claim 1, further comprising only two elongated hollow projections extending perpendicular to the head and provided with said only two openings for issuing the fluid in form of said only two pulsating jets.

* * * * *